United States Patent [19]

Baker et al.

[11] Patent Number: 4,808,600
[45] Date of Patent: Feb. 28, 1989

[54] FUNGICIDAL PYRIDYL CYCLOPROPANE CARBOXAMIDES

[75] Inventors: Don R. Baker, Orinda; Keith H. Brownell, San Jose, both of Calif.

[73] Assignee: Stauffer Chemical Co., Westport, Conn.

[21] Appl. No.: 193,621

[22] Filed: May 13, 1988

Related U.S. Application Data

[60] Division of Ser. No. 36,542, Apr. 15, 1987, Pat. No. 4,766,134, which is a continuation-in-part of Ser. No. 29,116, Mar. 23, 1987, abandoned, which is a continuation of Ser. No. 859,152, May 2, 1986, abandoned.

[51] Int. Cl.$^4$ .................... A01N 43/40; C07D 213/64
[52] U.S. Cl. ...................................... 514/346; 514/352; 546/292; 546/305; 546/309
[58] Field of Search .................... 546/292, 305, 309; 514/346, 352

[56] References Cited

PUBLICATIONS

Baker et al., Chemical Abstracts, vol. 108, No. 11, Abst. No. 108:94403g, Mar. 14, 1988.
Pilgram, Chemical Abstracts, vol. 92, No. 7, Abst. No. 92:58618y, Feb. 18, 1980.

*Primary Examiner*—Alan L. Rotman
*Attorney, Agent, or Firm*—Michael J. Bradley

[57] ABSTRACT

Novel fungicidal pyridyl cyclopropane carboxamides having the general structural formula

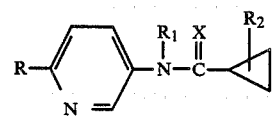

in which R is selected from the group halogen $C_1$–$C_3$ alkoxy and $C_1C_3$ haloalkoxy, $R_1$ is selected from the group of —H and —C≡N; and $R_2$ is selected from the group of —H, 1—$CH_3$ and 2—$CH_3$; X is O or S; and fungicidal acceptable organic and inorganic salts thereof. These compounds provide excellent control of fungal growth.

15 Claims, No Drawings

FUNGICIDAL PYRIDYL CYCLOPROPANE CARBOXAMIDES

CROSS-REFEREMCE TO RELATED APPLICATIONS

This application is a divisional of Ser. No. 07/036,542 filed 04-15-87, now U.S. Pat. No. 4,766,134, which is a continuation-in-part of Ser. No. 07/029,116 filed 03-23-87 (abandoned), which is a continuation of Ser. No. 06/859,152 filed 05-02-86 (abandoned).

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infestation, could destroy the fungi and eliminate the deleterious effects by use of a postinfestation curative spray.

SUMMARY OF THE INVENTION

Novel fungicidal pyridyl cyclopropane carboxamides having the formula

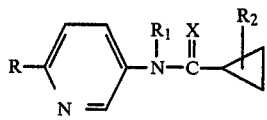

wherein R is selected from the group consisting of halogen such as chlorine, fluorine and bromine, preferably chlorine, $C_1$–$C_3$ alkoxy such as propoxy, ethoxy and methoxy, preferably methoxy, and $C_1$–$C_3$ haloalkoxy; $R_1$ is selected from the group consisting of hydrogen and cyano; $R_2$ is selected from the group consisting of methyl and hydrogen; X is either oxygen or sulfur; and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to a post-infection application of a fungicide which establishes control of fungal infection and prevents development of deleterious effects of the fungi on the host crop.

DETAILED DESCRIPTION

The novel fungicidal compounds of this invention are pyridyl cyclopropane carboxyamides having the general formula:

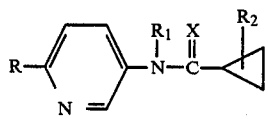

wherein R is selected from the group consisting of halogen such as chlorine, fluorine and bromine, preferably chlorine, $C_1$–$C_3$ alkoxy such as propoxy, ethoxy and methoxy, preferably methoxy, and $C_1$–$C_3$ haloalkoxy; $R_1$ is selected from the group consisting of hydrogen and cyano; and $R_2$ is selected from the group consisting of methyl and hydrogen; X is either oxygen or sulfur; and fungicidally acceptable organic and inorganic salts thereof.

By the term "halogen" is meant bromine, fluorine and chloride.

By the term "$C_1$–$C_3$ alkoxy" is meant methoxy, ethoxy, propoxy and isopropoxy.

By the term "$C_1$–$C_3$ haloalkoxy" is meant halogen substituted methoxy, ethoxy, propoxy and isopropoxy.

The compounds of this invention can be generally prepared by reacting a properly substituted 5-aminopyridine with a properly substituted cyclopropane carboxylic acid chloride in a polar solvent such as dichloromethane in a suitable reactor. It is desirable to maintain an acid scavenger such as pyridine in the reaction vessel. The reaction generally will proceed at room temperature but will operate at a temperature range from −30° to 60° C., depending on the substitutions on the amino pyridine and the cyclopropane carboxylic acid chloride. The reaction should go to completion within 1 to 3 hours. The resulting product is recovered in a conventional manner by washing with an alkali solution such as NaOH and water, drying over conventional drying agents such as magnesium sulfate, and crystallizing in hexane. The thiono carboxamides of this invention are also active. These compounds are prepared in general by reaction of the corresponding amide with phosphorous pentasulfide in a neutral solvent such as benzene, toluene, chloroform, methylenechloride or pyridine. The product is soluble in strong alkali and may be isolated from the reaction mixture in that manner by readjustment of the pH of the extract to neutrality. Salts of the various pyridyl cyclopropane carboxamides can be conventionally prepared by reacting at least a molar amount of a Lewis acid with the carboxamide. Preferably the reaction is run in a solvent for the carboxamide with heating if necessary. The prepared salt is recovered from the reaction mixture by conventional techniques.

Pyridyl carboxamides of the invention are basic. The unprotonated nitrogen atom of the pyridyl ring can be protonated by an acid, either organic or inorganic. Representative inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of N-(2-Methoxy-5-pyridyl)-cyclopropane carboxamide

5-Amino-2-methoxy pyridine (12.4 grams, 0.10 mole) and 10 milliliters (ml) of pyridine were mixed together in 200 ml dichloromethane in a reaction flask. 9.1 ml (0.10 mole) of cyclopropane carboxylic acid chloride was added to the reaction mixture over a period of 2 minutes. The reaction was exothermic and temperature rose to 34° C. The reaction was allowed to stand for one hour at room temperature, after which the reaction mixture was washed with 200 ml of 5% sodium hydroxide and 100 ml of water. The resulting organic phase was separated and dried over anhydrous magnesium sulfate. Crystals formed, so that mixture was filtered and washed with 300 ml of acetone and the filtrate evaporated in vacuo to give a solid that was triturated with hexane to yield 16.7 grams, after drying. The product was identified by IR and NMR as the title compound, having a melting point of 130°–131° C. This compound will be referred to as Compound 1.

EXAMPLE 2

Preparation of N-(2-Methoxy-5-pyridyl)-cyclopropane carboxamide dodecanoic acid salt Three grams (0.016 mole) of the compound of Example 1 was dissolved in 100 ml of acetone in a 300 ml, one-neck, round-bottom flask by swirling. 3.2 g (0.016 mole) dodecanoic acid was added which went into solution. The resulting solution was evaporated on a rotary evaporator, yielding 6.2 g, of a white solid having a melting point of 92°–96° C., which was identified by nuclear magnetic resonance spectroscopy as the title compound. This compound will be known as Compound 7.

EXAMPLE 3

Preparation of N-(2-methoxy-5-pyridyl)-cyclopropanethiocarboxamide

A solution of 5.0 g of N-(2-methoxy-5-pyridyl)-cyclopropanecarboxamide (0.0.026 moles) in methylene chloride (100 ml) was refluxed with stirring with 6.1 g of phosphorous pentasulfide (0.03 moles). The reaction mixture was cooled to room temperature and diluted with chloroform (100 ml) and washed with a saturated sodium bicarbonate solution (200 ml). The organic phase was extracted with 5% sodium hydroxide solution (2×100 ml). This extract was acidified with concentrated hydrochloric acid to pH 7 and extracted with chloroform (3×100 ml). This chloroform extract was dried over magnesium sulfate and evaporated in vacuo to yield 0.6 g of the desired product having a melting point of 79°–83° C.

Representative compounds of this invention and their physical properties are shown in Table I.

TABLE I

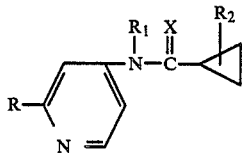

| Cmpd. No. | R | $R_1$ | $R_2$ | X | $n_D^{30}$ or melting point °C. |
|---|---|---|---|---|---|
| 1 | —OCH₃ | —H | —H | O | 130.0–131.0 |
| 2 | —Cl | —H | —H | O | 167.0–169.0 |
| 3 | —OCH₃ | —C≡N | —H | O | 84.0–92.0 |
| 4 | —OCH₃ | —H | 1-CH₃ | O | 70.0–74.0 |
| 5 | —OCH₃ | —H | 2-CH₃ | O | 66.0–70.0 |
| 6 | hydrochloric acid salt of Cmpd. 1 | | | | 144.0–146.0 |
| 7 | dodecanoic acid salt of Cmpd. 1 | | | | 92.0–96.0 |
| 8 | 2-naphthalene-sulfonic acid salt of Cmpd. 1 | | | | 90.0–96.0 |
| 9 | acetic acid salt of Cmpd. 1 | | | | 112.0–120.0 |
| 10 | benzoic acid salt of Cmpd. 1 | | | | 78.0–85.0 |
| 11 | chloromethyl-phosphonic acid salt of Cmpd. 1 | | | | 110.0–118.0 |
| 12 | hydrochloric acid salt of Cmpd. 2 | | | | 134.0–136.0 |
| 13 | —Br | —H | —H | O | 172.0–175.0 |
| 14 | phenyl phosphonic acid salt of Cmpd. 1 | | | | 108.0–115.0 |

TABLE I-continued

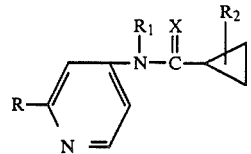

| Cmpd. No. | R | $R_1$ | $R_2$ | X | $n_D^{30}$ or melting point °C. |
|---|---|---|---|---|---|
| 15 | sulfamic acid salt of Cmpd. 1 | | | | 131.0–136.0 |
| 16 | trifluoroacetic acid salt of Cmpd. 1 | | | | 89.0–93.0 |
| 17 | nitric acid salt of Cmpd. 1 | | | | 144.0–145.0 |
| 18 | —OCH₃ | —H | —H | S | 79.0–83.0 |
| 19 | —F | —H | —H | O | 116.0–117.0 |

EXAMPLE 3

Mole Equivalent Preventative Spray Evalution Procedures Barley Powdery Mildew (PM)

Northrup King Sunbar 401 barley seed is planted (12 seeds/2" pot) in a sandy-loam soil seven days prior to testing. The test compound is diluted in a 50/50 acetone/water solution to produce concentrations decreasing from 0.004 molar. The test solution is then sprayed onto the barley plants with atomizing sprayers.

Twenty-four hours later, test plants are placed in an inoculation box equipped with a circulating fan. Barley plants with heavily sporulating *Erysiphe gramins* lesions are placed in front of the fan to dislodge and distribute the spores. After two minutes the fan is shut off and the chamber is left closed five minutes for the spores to settle. Inoculated plants are then placed on an automatic sub-irrigation green-house bench.

Results are recorded seven days following inoculation as percent disease control based on the percent reduction in lesion area as compared to the untreated control plants. Compound concentrations which provide 90% disease control (CO 90) are determined from dosage/dilution curves.

Leaf Rust (LR)

Seven seeds of Anza wheat are planted in 2" pots in a sandy-loam soil 12 days prior to testing. The compound to be tested is diluted with a 50/50 acetone/water solution to produce concentrations decreasing from 0.004 molar. Twelve ml of test solution are sprayed onto the wheat plants with an atomizing sprayer.

A suspension of *Puccinia recondita* urediospores is prepared by vacuuming spores from wheat leaves with ureida pustules and suspending 10⁵ spores/ml in deionized water plus 0.5% Tween ® 20 (polyoxyethylene sorbitan monolaurate). Plants are inoculated 24 hours after treatment by spraying with the spore suspension to runoff, allowing it to dry on the leaves, respraying to runoff, and then placing the plants into a dark mist chamber. Following 48 hours in the mist, plants are moved to a subirrigation greenhouse bench.

Results are recorded ten days following inoculation as percent disease control based on the percent reduction in lesion areas as compared to the untreated control plants. Compound concentrations which provide 90% disease control (EC 90) are determined from dosage/dilution curves.

Botrytis Bud Blight (BB)

Two white rose petals are placed in a petri dish lined with wet filter paper. The compound to be tested is diluted with a 50/50 acetone/water solution to produce concentrations decreasing from 0.004 molar. On half ml of test solution is atomized onto the petals, and allowed to dry.

Inoculum is prepared by adding a 5 mm plug from a two-week old *Botrytis cineria* culture grown on Elliot's V-8 agar, to 10 ml sterile distilled water plus 0.5% grape juice. A 20 ul drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

The molar equivalent of 0.004 used as the initial dilution in these evaluation procedures is equivalent to 750 parts per million (ppm) of the amides. All salts tested were adjusted in a solution to 0.004 molar which is equivalent to the 750 ppm of the amide from which the salt was made.

The results are presented in Table II as an approximate EC 90 in parts per million. The entry (750) indicates partial control at 750 ppm.

TABLE II

| Cmpd. No. | PM | LR | BB |
| --- | --- | --- | --- |
| 1 | 200 | 200 | 20 |
| 2 | 250 | 750 | 25 |
| 3 | (750) | 500 | 25 |
| 4 | >750 | >750 | 750 |
| 5 | (750) | 200 | 200 |
| 6 | 200 | 200 | 70 |
| 7 | 200 | 200 | 20 |
| 8 | 200 | 200 | 20 |
| 9 | 200 | 200 | 20 |
| 10 | 200 | 200 | 20 |
| 11 | 200 | 200 | 20 |
| 12 | — | — | 80 |
| 13 | (750) | (750) | (750) |
| 14 | 200 | 200 | 20 |
| 15 | — | — | 20 |
| 16 | — | — | 20 |
| 17 | — | — | 20 |
| 18 | (750) | (750) | 20 |
| 19 | (750) | 250 | 80 |

EXAMPLE 4

Post-Infection Fungicide Screening Procedures

Apple Scab (AS)

Apple seedlings are inoculated by spraying the foliage with *Venturia inaequalis* using standard procedures 24 hours. Following inoculation the test compound is applied in solution as a foliage spray at the rate of 160 mg/l. Results are determined after sympton development from the reduction in lesion area as compared to the untreated control plants.

Rice Blast (RB)

Six days before inoculation, seedling rice plants are drenched with a solution containing 50 mg test compound/liter of soil. Inoculation with *Piricularia oryzae* is performed using standard procedures. Results are determined after sympton development from the reduction in lesion area as compared to the untreated control plants.

Wheat Blume Blotch (GB)

Two days before inoculation, the test compound is applied in solution to wheat seedlings as a foliage spray at the rate of 500 mg/l. Inoculation with *Septoria nodorum* is performed using standard procedures. Results are determined after sympton development from the reduction in lesion area as compared to the untreated control plants.

Wheat Foot Rot (FR)

Wheat seed infested with *Fusarium culmorum* is treated with 500 mg/kg of test compound using standard methods. Results are determined after sympton development from the reduction in disease as compared to the untreated control plants.

Activity is reported on the following basis: 0=nil; X=light; XX=moderate and XXX=high.

TABLE III

| Cmpd. No. | Disease | | | |
| --- | --- | --- | --- | --- |
| | AS | RB | GB | FR |
| 1 | XXX | X | XX | X |
| 2 | 0 | X | 0 | X |

EXAMPLE 5

CURATIVE SPRAY EVALUATION PROCEDURES

Leaf Rust (LR)

Seven seeds of Anza wheat are planted in 2" pots in a sandy loam soil 12 days prior to testing. A suspension of *Puccinia recondita* urediospores is prepared by vacuuming spores from wheat leaves with uredia pustules and suspending $10^5$ spores/ml in deionized water plus 0.5% Tween ® 20 (polyoxyethylene sorbitan monolaurate). Plants are inoculated by spraying with the spore suspension to runoff, allowing it to dry on the leaves, respraying to runoff, and then placing the plants into a mist chamber. Following 48 hours in the mist, plants are moved to a subirrigation greenhouse bench.

The compound to be tested is diluted in a 50/50 acetone/water solution to produce concentrations decreasing from 0.075%. Fifty hours following inoculation, the plants are placed on a rotating turntable and sprayed with the test solution to near runoff with atomizing nozzles. (Time of inoculation is defined as when plants are placed into the mist chamber.)

Results are recorded ten days following inoculation as percent disease control based on the percent reduction in lesion area as compared to the untreated control plants.

TABLE III

| Cmpd. No. | LR |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |

The compounds of this invention are particularly effective against Botrytis Bud Blight and are particularly effective as preventive foliar sprays and curative foliar sprays when compared to standard commercial compounds used as Botrytis preventative and curative sprays. Fungi on which the compounds of the present invention are particularly effective are as follows: *Botrytis cinerea; Venturia inaequalis; Septoria nodorum; Erysiphe graminis; Fusarium culmorum; Piricularia oryzae;* and *Puccinia graminis.*

The compounds of the present invention are useful as fungicides, especially as preventative or curative fungicides, and can be applied in a variety of ways at various concentrations. In general, these compounds and formulations of these compounds can be applied directly to the crop foliage, the soil in which the crop is growing, or in the irrigation water for the crop or soil. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plant either as a dry dust or as a dispersion in water or other liquid. Typical carrier for wettable powders include fuller's earth, kaolin clays, silicas and other readily wet organic or inorganic diluents. Wettable powders normally are prepared to contain about 5% to about 95% of the active ingredient and usually also contain a smalll amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil or plant as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

SUMMARY OF TYPICAL FORMULATIONS

| Ingredient | Weight % | | |
|---|---|---|---|
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:
1. A compound having the structural formula

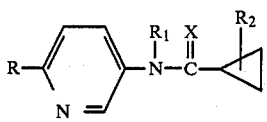

in which R is selected from the group consisting of $C_1$-$C_3$ alkoxy and $C_1$-$C_3$ haloalkoxy, $R_1$ is —H; and $R_2$ is selected from the group consisting of —H, 1—$CH_3$ and 2—$CH_3$; X is O or S; or a fungicidally acceptable organic or inorganic salt thereof.

2. The compound of claim 1 wherein R is selected from the group consisting of $C_1$-$C_3$ alkoxy and $C_1$-$C_3$ haloalkoxy; $R_1$ is —H; and $R_2$ is selected from the group consisting of —H, 1—$CH_3$ and 2—$CH_3$; X is O or a fungicidally acceptable organic or inorganic salt thereof.

3. The compound of claim 2 wherein R is —$OCH_3$, $R_1$ is —H and $R_2$ is —H.

4. The compound of claim 2 wherein R is $C_1$-$C_3$ haloalkoxy, $R_1$ is —H and $R_2$ is —H.

5. The compound of claim 1 wherein R is $OCH_3$, $R_1$ is —H, $R_2$ is —H and X is —S.

6. The compound of claim 1 wherein R is —$OCH_3$, $R_1$ is —H and $R_2$ is 1—$CH_3$.

7. The compound of claim 1 wherein R is $OCH_3$, $R_1$ is —H and $R_2$ is 2—$CH_3$.

8. A fungicidal composition comprising a fungicidally effective amount of a compound having the structural formula

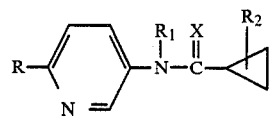

in which R is selected from the group consisting of $C_1$-$C_3$ alkoxy and $C_1$-$C_3$ haloalkoxy, $R_1$ is —H; and $R_2$ is selected from the group consisting of —H, 1—$CH_3$ and 2—$CH_3$; is O or S; or a fungicidally acceptable organic or inorganic salt thereof, and an inert diluent carrier therefor.

9. The method of controlling fungi comprising applying to the area where control is desired, a fungicidally effective amount of a compound having the formula

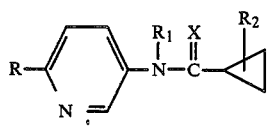

in which R is selected from the group consisting of $C_1$-$C_3$ alkoxy and $C_1$-$C_3$ haloalkoxy, $R_1$ is —H; and $R_2$ is selected from the group consisting of —H, 1—$CH_3$ and 2—$CH_3$; X is O or S; or a fungicidally acceptable organic or inorganic salt thereof.

10. The method of claim 9 wherein R is selected from the group consisting of $C_1$-$C_3$ alkoxy and $C_1$-$C_3$ haloalkoxy; $R_1$ is —H; and $R_2$ is selected from the group consisting of —H, 1—$CH_3$ and 2—$CH_3$; X is O or a fungicidally acceptable organic or inorganic salt thereof.

11. The method of claim 10 wherein $R_1$ is —H and $R_2$ is —H.

12. The method of claim 10 wherein R is $C_1$-$C_3$ haloalkoxy.

13. The method of claim 10 wherein R is $OCH_3$.

14. The method of claim 10 wherein R is —$OCH_3$, $R_1$ is —H and $R_2$ is 1—$CH_3$.

15. The method of claim 10 wherein R is $OCH_3$, $R_1$ is —H and $R_2$ is 2—$CH_3$.

* * * * *

UNITED STATES PATENT AND TRADEMARK OFFICE
CERTIFICATE OF CORRECTION

PATENT NO. : 4,808,600

DATED : February 28, 1989

INVENTOR(S) : Don R. Baker and Keith H. Brownell

It is certified that error appears in the above-identified patent and that said Letters Patent is hereby corrected as shown below:

In Column 10, at line 11, after "2-$CH_3$;" please insert

--- X ---

Signed and Sealed this

Twenty-third Day of January, 1990

Attest:

JEFFREY M. SAMUELS

Attesting Officer     Acting Commissioner of Patents and Trademarks

REEXAMINATION CERTIFICATE (1713th)

United States Patent [19]
Baker et al.

[11] B1 4,808,600
[45] Certificate Issued Jun. 2, 1992

[54] FUNGICIDAL PYRIDYL CYCLOPROPANE CARBOXAMIDES

[75] Inventors: Don R. Baker, Orinda; Keith H. Brownell, San Jose, both of Calif.

[73] Assignee: ICI Americas Inc., Wilmington, Del.

Reexamination Request:
No. 90/002,333, Apr. 26, 1991

Reexamination Certificate for:
Patent No.: 4,808,600
Issued: Feb. 28, 1989
Appl. No.: 193,621
Filed: May 13, 1988

Certificate of Correction issued Jan. 23, 1990.

Related U.S. Application Data

[60] Division of Ser. No. 36,542, Apr. 15, 1987, Pat. No. 4,766,134, which is a continuation-in-part of Ser. No. 29,116, Mar. 23, 1987, abandoned, which is a continuation of Ser. No. 859,152, May 2, 1986, abandoned.

[51] Int. Cl.$^5$ .................. A01N 43/40; C07D 213/64
[52] U.S. Cl. .................................. 514/346; 514/352; 546/292; 546/305; 546/309
[58] Field of Search ............... 546/292, 305, 309; 514/346, 352

[56] References Cited

U.S. PATENT DOCUMENTS

| | | | |
|---|---|---|---|
| 3,277,107 | 10/1966 | Neighbors | 548/195 |
| 3,277,171 | 10/1966 | Hopkins | 564/190 |
| 3,467,753 | 9/1969 | Foster et al. | 514/349 |
| 3,493,555 | 2/1970 | Wilbert et al. | 534/773 |
| 4,672,070 | 6/1987 | Takahashi et al. | 514/346 |

Primary Examiner—Alan L. Rotman

[57] ABSTRACT

Novel fungicidal pyridyl cyclopropane carboxamides having the general structural formula

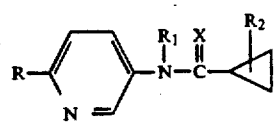

in which R is selected from the group halogen $C_1$-$C_3$ alkoxy and $C_1C_3$ haloalkoxy, $R_1$ is selected from the group of —H and —C≡N; and $R_2$ is selected from the group —H, 1—$CH_3$ and 2—$CH_3$, X is O or S; and fungicidal acceptable organic and inorganic salts thereof. These compounds provide excellent control of fungal growth.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 8–10 are determined to be patentable as amended.

Claims 3–7 and 11–15, dependent on an amended claim, are determined to be patentable.

New claims 16 and 17 are added and determined to be patentable.

1. A compound having the structural formula

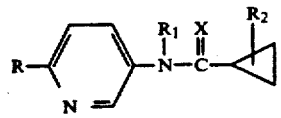

in which R is selected from the group consisting of [$C_1$–$C_3$ alkoxy] *methoxy* and $C_1$–$C_3$ haloalkoxy, $R_1$ is —H; and $R_2$ is selected from the group consisting of —H, 1—$CH_3$ and 2—$CH_3$; X is O or S; or a fungicidally acceptable organic or inorganic salt thereof.

2. The compound of claim 1 wherein R is selected from the group consisting of [$C_1$–$C_3$ alkoxy] $C_1$–$C_3$ haloalkoxy, $R_1$ is —H; and $R_2$ is selected from the group *methoxy* and consisting of —H, 1—$CH_3$ and 2—$CH_3$ and 2—$CH_3$; X is O; or a fungicidally acceptable organic or inorganic salt thereof.

8. A fungidical composition comprising a fungicidally effective amount of a compound having the structural formula

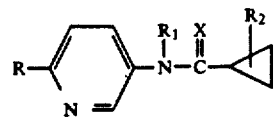

in which R is selected from the group consisting of [$C_1$–$C_3$ alkoxy] *methoxy* and $C_1$–$C_3$ haloalkoxy, $R_1$ is —H; and $R_2$ is selected from the group consisting of —H, 1—$CH_3$ and 2—$CH_3$; X is O or S; or a fungicidally acceptable organic or inorganic salt thereof, and an inert diluent carrier therefor.

9. The method of controlling fungi comprising applying to the area where control is desired, a fungicidally effective amount of a compound having the formula

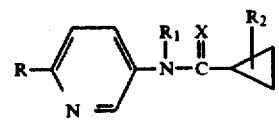

in which R is selected from the group consisting of [$C_1$–$C_3$ alkoxy] *methoxy* and $C_1$–$C_3$ haloalkoxy, $R_1$ is —H; and $R_2$ is selected from the group consisting of —H, 1—$CH_3$ and 2—$CH_3$; X is O or S; or a fungicidally acceptable organic or inorganic salt thereof.

10. The method of claim 9 wherein R is selected from the group consisting of [$C_1$–$C_3$ alkoxy] *methoxy* and $C_1$–$C_3$ haloalkoxy, $R_1$ is —H; and $R_2$ is selected from the group consisting of —H, 1—$CH_3$ and 2—$CH_3$; X is O or a fungicidally acceptable organic or inorganic salt thereof.

*16. The compound N-(2-methoxy-5-pyridyl)-cyclopropane carboxamide.*

*17. A fungicidal composition comprising a fungicidally effective amount of N-(2-methoxy-5-pyridyl)-cyclopropane carboxamide and an inert diluent carrier.*

* * * * *